(12) United States Patent
Han (10) Patent No.: US 10,136,874 B2
(45) Date of Patent: Nov. 27, 2018

(54) X-RAY IMAGING APPARATUS

(71) Applicant: VIEWORKS CO., LTD., Gyeonggi-do (KR)

(72) Inventor: Dong Kook Han, Gyeonggi-do (KR)

(73) Assignee: Vieworks Co., Ltd., Anyang-si, Gyeonggi-do (KR)

( * ) Notice: Subject to any disclaimer, the term of this patent is extended or adjusted under 35 U.S.C. 154(b) by 206 days.

(21) Appl. No.: 15/180,407

(22) Filed: Jun. 13, 2016

(65) Prior Publication Data

US 2016/0366755 A1 Dec. 15, 2016

(30) Foreign Application Priority Data

Jun. 12, 2015 (KR) ........................ 10-2015-0083160

(51) Int. Cl.
*H05G 1/26* (2006.01)
*A61B 6/00* (2006.01)
*H05G 1/44* (2006.01)

(52) U.S. Cl.
CPC ............ *A61B 6/542* (2013.01); *A61B 6/4233* (2013.01); *H05G 1/44* (2013.01)

(58) Field of Classification Search
None
See application file for complete search history.

(56) References Cited

U.S. PATENT DOCUMENTS

2004/0156473 A1* 8/2004 Nonaka .................... H05G 1/26
378/62
2014/0185764 A1* 7/2014 Takenaka ................. A61B 6/42
378/62

FOREIGN PATENT DOCUMENTS

| EP | 0849980 B1 | 6/1998 |
| JP | 4383899 B2 | 12/2009 |
| JP | 2013033030 A | 2/2013 |
| KR | 101126582 B1 | 3/2012 |
| KR | 101147422 B1 | 5/2012 |
| KR | 1020140148248 A | 12/2014 |
| KR | 1020150039506 A | 4/2015 |

* cited by examiner

*Primary Examiner* — Hoon Song
(74) *Attorney, Agent, or Firm* — Saliwanchik, Lloyd & Eisenschenk (57) ABSTRACT

The present invention relates to an X-ray imaging apparatus that includes a bias voltage source that provides a bias voltage to pixels that detect X-rays and an automatic exposure control (AEC) processing unit that detects a current flowing between the bias voltage source and the pixels and outputs an AEC signal.

13 Claims, 7 Drawing Sheets

X-RAY IMAGING APPARATUS

CROSS-REFERENCE TO RELATED APPLICATION

This application claims priority under 35 U.S.C. § 119 to Korean Patent Application No. 10-2015-0083160, filed Jun. 12, 2015, which is hereby incorporated by reference in its entirety.

BACKGROUND

Field of the Invention

The present invention relates to an X-ray imaging apparatus, and more particularly, to an X-ray imaging apparatus having an automatic exposure control (AEC) function.

Discussion of Related Art

Generally, an X-ray imaging system includes an X-ray generator that generates X-rays and irradiates X-rays to a subject and an X-ray imaging apparatus that detects the X-rays transmitted through the subject.

Furthermore, a recent X-ray imaging system includes an automatic exposure control (AEC) unit to link operations of the X-ray generator and the X-ray imaging apparatus to minimize a subject's exposure to the X-rays.

That is, when X-ray irradiation time is longer than necessary, damage due to overexposure to radiation may occur, while on the contrary, when a subject is exposed to an amount of X-rays that is too small, quality of image may be lowered, and thus a case may occur in which the obtained image is scrapped and an image is taken again.

In other words, the AEC unit detects an amount of X-ray exposure and outputs an AEC signal to the X-ray generator so that the X-ray generator may decide whether or not to stop emitting X-rays.

To detect such an amount of X-ray exposure, the AEC unit is generally installed at the X-ray imaging apparatus, and an amount of X-ray exposure is normally detected by an AEC ionization chamber separately provided between a scintillator and a subject.

Meanwhile, the related art of the present invention was disclosed in Korean Laid-open Patent Publication No. 10-2015-0039506 (2015 Apr. 10).

BRIEF SUMMARY

However, when a separate ionization chamber is used in the same manner as a conventional automatic exposure control (AEC) apparatus, there are problems in that quality of an X-ray image may be lowered due to the ionization chamber and a separate system capable of detecting X-rays has to be provided for AEC.

Accordingly, although designing AEC sensors installed in a pixel array of the X-ray imaging apparatus are being considered, there are problems of increased complexity of the system, process cost, and failure rate.

That is, an operation of an X-ray detector may be classified into an integration process, a readout process, and the like. Although reading an electrical signal output from pixels through a gate driver, a readout circuit, and the like is performed in the readout process, an AEC is performed in the integration process, and the gate driver or the readout circuit is generally not operated during the integration process. Accordingly, a design of an additional circuit for operating the gate driver or the readout circuit in the integration process to perform the AEC using the AEC sensor provided in the pixel array is needed, and complexity of the system increases due to such a design.

The present invention is directed to providing an X-ray imaging apparatus that perform an AEC function without adding an additional apparatus or a complex circuit.

According to an aspect of the present invention, there is provided an X-ray imaging apparatus including a bias voltage source that provides a bias voltage to pixels that detect X-rays, and an automatic exposure control (AEC) processing unit that detects a current flowing between the bias voltage source and the pixels and outputs an AEC signal.

The bias voltage source may provide the bias voltage to photodiodes included in the pixels through a common electrode, and the AEC processing unit may detect a current flowing between the common electrode and the bias voltage source.

The AEC processing unit may include: a detector that detects the current and converts the current into a voltage signal; and an output unit that outputs an AEC signal depending on a voltage output by the detector.

The output unit may include an integrator that integrates the voltage and outputs a voltage according to an integration result, and a comparator that compares the voltage according to the integration result and a reference value and outputs the comparison result as the AEC signal.

The output unit may include an integrator that integrates the voltage and outputs a voltage according to the integration result; and an amplifier that amplifies the voltage according to the integration result and outputs the amplified voltage as the AEC signal.

The output unit may further include a compensator that compensates for an output of the integrator due to an offset of the current.

The compensator may provide a voltage corresponding to an output value of the detector corresponding to an offset of the current to any one of input electrodes of the integrator.

The output unit may further include an offset processor that offsets the voltage according to the integration result by an offset voltage due to the compensator.

The detector may include a switch that allows bypassing the current.

The switch may be opened or closed depending on an operation state of an X-ray detector.

The common electrode may be classified into a plurality of groups, and the AEC processing unit may be included in each of the groups.

BRIEF DESCRIPTION OF THE DRAWINGS

The above and other objects, features and advantages of the present invention will become more apparent to those of ordinary skill in the art by describing exemplary embodiments in detail with reference to the accompanying drawings, in which.

DETAILED DESCRIPTION

Hereinafter, one embodiment of an X-ray imaging apparatus according to the present invention will be described with reference to accompanying drawings. In the specification, thicknesses of the drawings, sizes of components, and the like can be illustrated with exaggerations for clarity and convenience of description. In addition, some terms described below are defined by considering functions of the invention, and meanings may vary depending on, for example, a user's or an operator's intentions or customs. Therefore, the meanings of terms should be interpreted based on the content throughout this specification.

Figure 1:
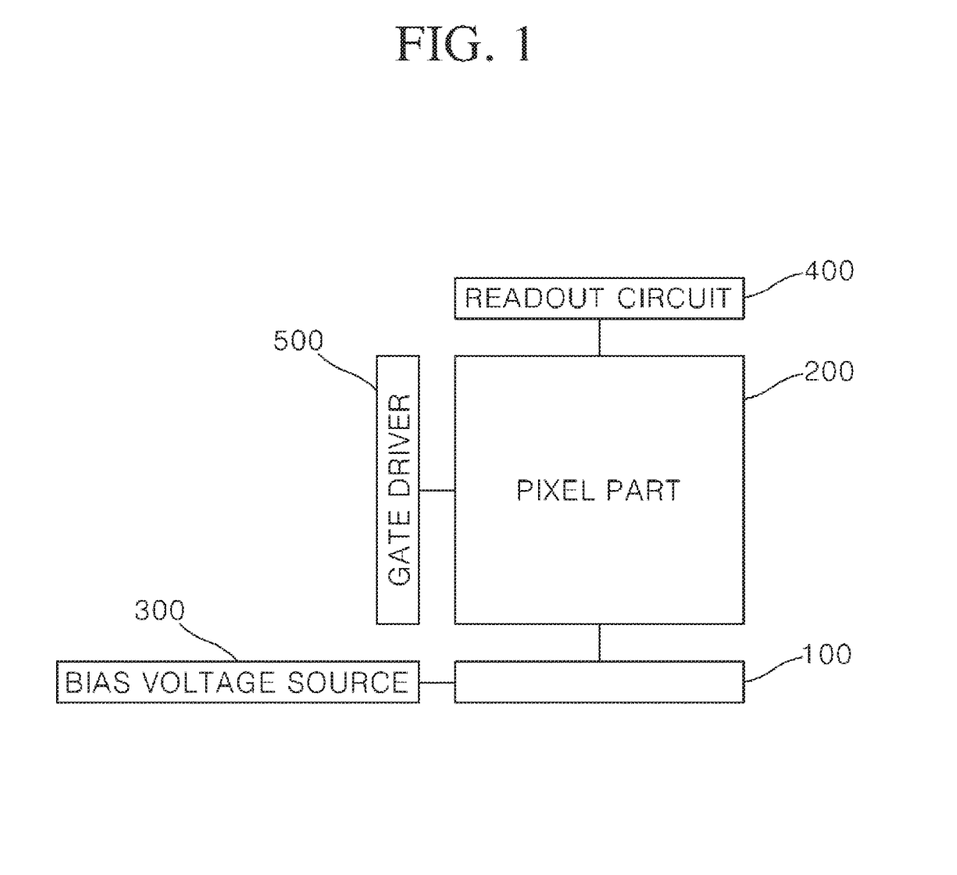
FIG. 1 is a block diagram illustrating a configuration of an X-ray imaging apparatus according to one embodiment of the present invention.
Figure 2:
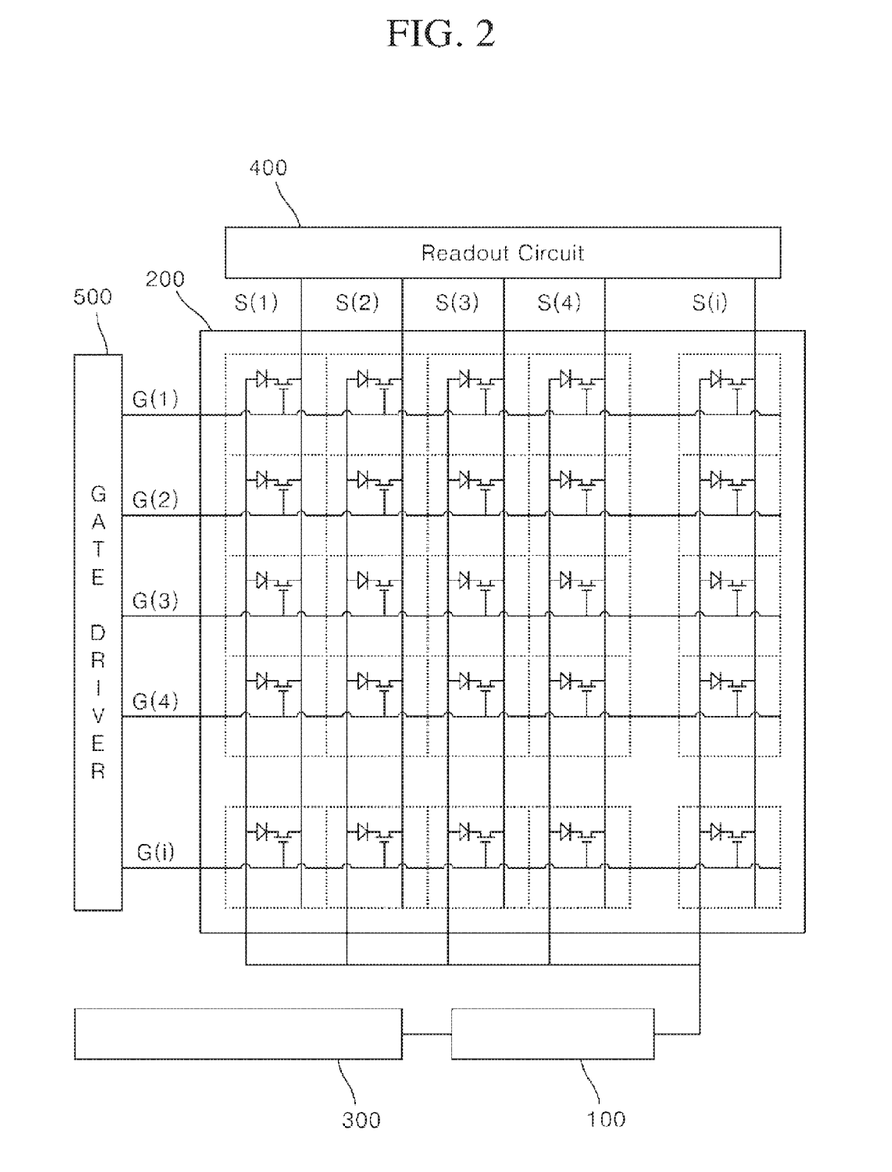
FIG. 2 is a schematic view for describing the configuration of the X-ray imaging apparatus according to one embodiment of the present invention.

FIG. 1 is a block diagram illustrating a configuration of an X-ray imaging apparatus according to one embodiment of the present invention, FIG. 2 is a schematic view for describing the configuration of the X-ray imaging apparatus according to one embodiment of the present invention, and the X-ray imaging apparatus will be described as follows with reference to the drawings.

As illustrated in FIG. 1, the X-ray imaging apparatus according to one embodiment of the present invention may include an AEC processing unit 100, a pixel part 200, a bias voltage source 300, a readout circuit 400, and a gate driver 500.

The pixel part 200 may include at least one pixel that detects X-rays. That is, a plurality of pixels in a matrix shape are provided in a general X-ray detector, such pixels are named as a pixel array, sensor array, or the like, and a set of such pixels is defined as the pixel part 200 in the embodiment.

Each pixel of the pixel part 200 may include a photodiode to detect X-rays. That is, when a scintillator or phosphor disposed in front of the pixel part 200 absorbs X-rays and emits visible light, the photodiode of each pixel converts the visible light to a photocurrent proportional to an amount of the visible light, and the X-rays may be detected by measuring the converted photocurrent.

In addition, as shown in FIG. 2, each of the photodiodes of the pixels (one end of each of the photodiodes of the pixels) may be connected to one common electrode, and such a common electrode may be connected to the bias voltage source 300 that supplies a bias voltage.

That is, the bias voltage source 300 may supply a bias voltage to each of the pixels through the common electrode.

In addition, the other end of each of the photodiodes may be connected to a drain of the individual transistor, and a source of each of the transistors may be connected to the readout circuit 400.

That is, the readout circuit 400 may collect electrical signals output by the photodiodes through the transistors, and the gate driver 500 may sequentially select one column through which the signals are to be collected by the readout circuit.

In other words, in a readout process of an X-ray detector, the gate driver 500 sequentially selects one column among the pixels of the pixel part 200, and the readout circuit 400 may collect signals from the pixels of the selected column.

Figure 4:
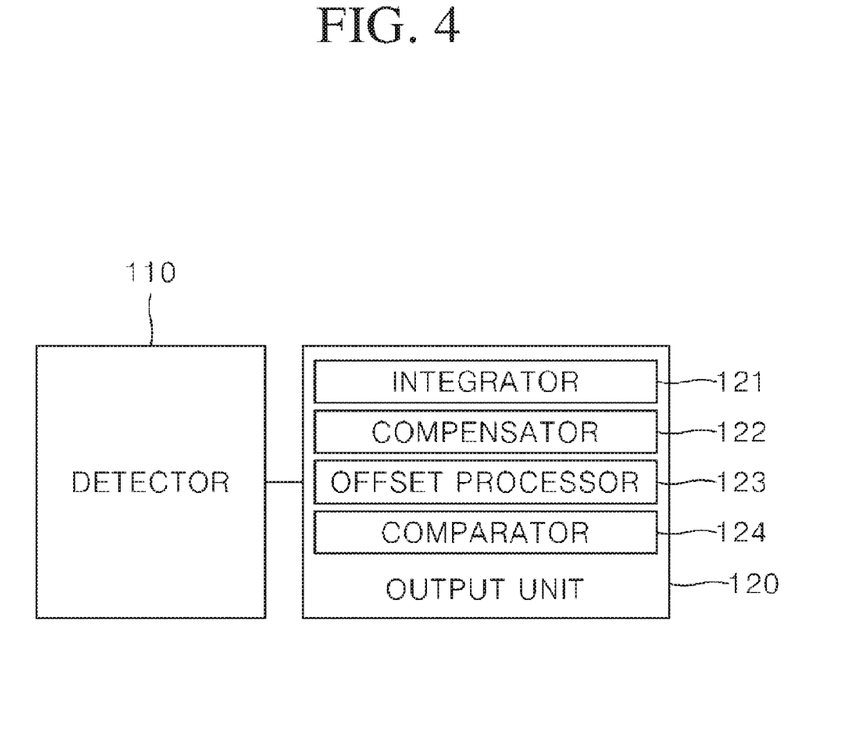
FIG. 4 is a schematic view for illustrating an automatic exposure control (AEC) processing unit of the X-ray imaging apparatus according to one embodiment of the present invention.
Figure 5:
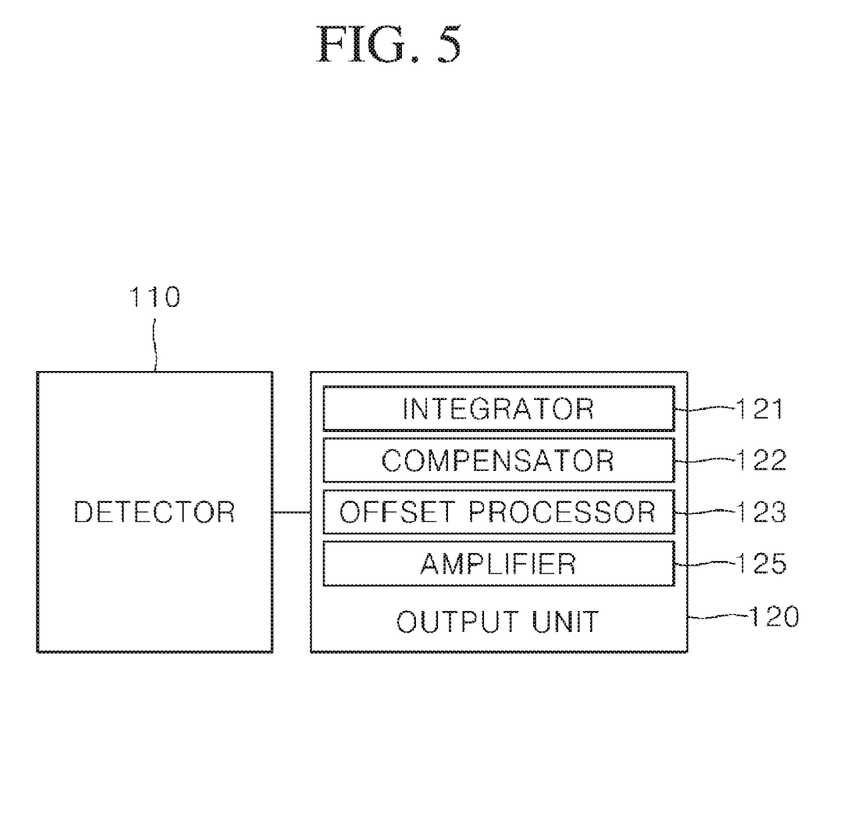
FIG. 5 is another schematic view for describing the AEC processing unit of the X-ray imaging apparatus according to one embodiment of the present invention.
Figure 6:
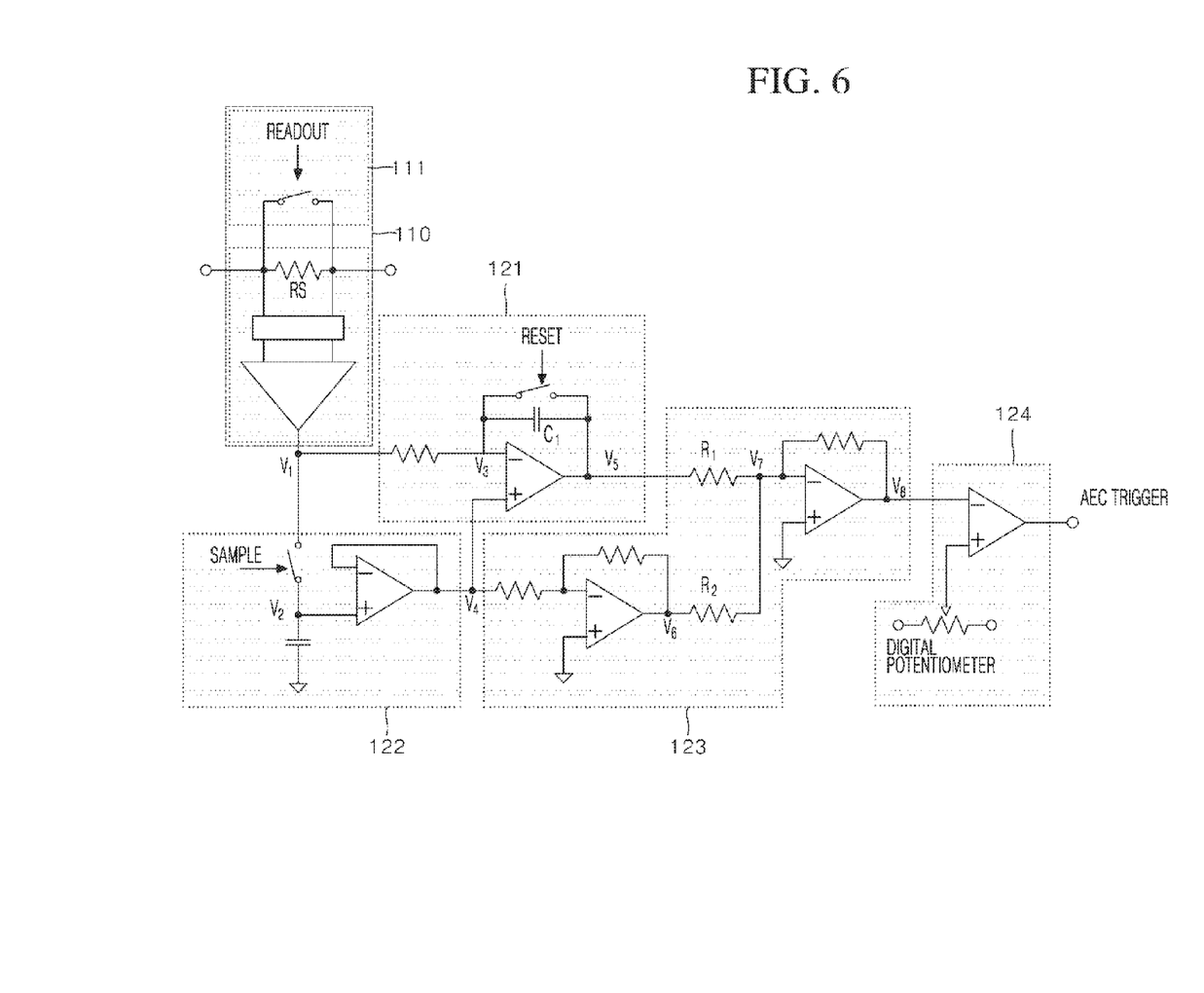
FIG. 6 is a circuit diagram for describing the AEC processing unit of the X-ray imaging apparatus according to one embodiment of the present invention.
Figure 7:
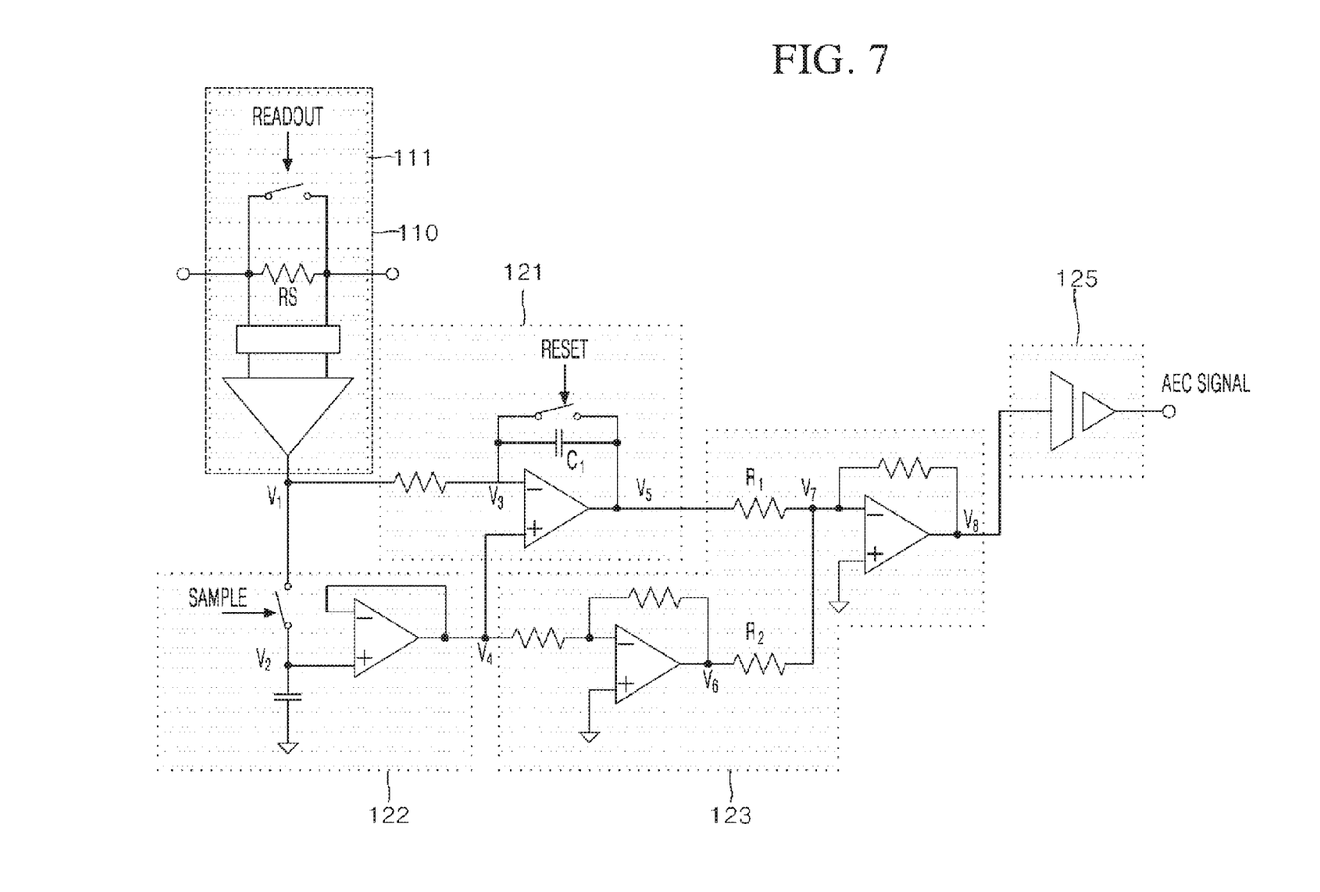
FIG. 7 is another circuit diagram for describing the AEC processing unit of the X-ray imaging apparatus according to one embodiment of the present invention.

FIG. 4 is a schematic view for illustrating AEC processing unit of the X-ray imaging apparatus according to one embodiment of the present invention, FIG. 5 is another schematic view for describing the AEC processing unit of the X-ray imaging apparatus according to one embodiment of the present invention, FIG. 6 is a circuit diagram for describing the AEC processing unit of the X-ray imaging apparatus according to one embodiment of the present invention, FIG. 7 is another circuit diagram for describing the AEC processing unit of the X-ray imaging apparatus according to one embodiment of the present invention, and the AEC processing unit of the X-ray imaging apparatus will be described as follows with reference to the drawings.

As illustrated in FIG. 4, the AEC processing unit according to one embodiment of the present invention includes a detector 110 and an output unit 120. In addition, the output unit 120 may include an integrator 121, a compensator 122, an offset processor 123, and a comparator 124.

The detector 110 may detect a current flowing between the bias voltage source 300 and the common electrode and convert the detected current to a voltage signal. For example, the detector 110 may include resistors and differential amplifiers to detect a current flowing between the bias voltage source 300 and the common electrode and convert the detected current to a voltage.

When the photodiode absorbs visible light emitted by a scintillator or phosphor and a photocurrent is generated, voltages of both electrodes of the photodiode are changed and a voltage $V_{ds}$ between the source and the drain of the transistor is also changed accordingly. When the $V_{ds}$ is changed as described above, an amount of leakage current is also changed depending on a level of the change. In addition, although most of visible light is absorbed by the photodiode, a very small amount of light is absorbed by the transistor due to a design limitation of a pixel structure, and the amount of the leakage current of the transistor is increased accordingly. That is, the amount of the leakage current of the transistor is changed depending on an amount of X-rays detected by the photodiode, and the total amount of the transistor leakage current that flow in the pixels is equal to an amount of current flowing between the common electrode and the bias voltage source 300.

Accordingly, when the amount of the current flowing to the common electrode is measured, an amount of X-ray exposure may be estimated even when the readout circuit 400 does not collect signals from the pixel part 200 by driving the gate driver 500.

The output unit 120 may output an AEC signal depending on a voltage output by the detector 110. Here, the AEC signal refers to a control signal to determine whether emission of X-ray is stopped, and the output unit 120 may output such a control signal to a controller and the like of the X-ray imaging system.

Here, the output unit 120 may include the integrator 121, the compensator 122, the offset processor 123, and the comparator 124 and output an AEC signal depending on a voltage output by the detector 110.

The integrator 121 may integrate the voltage output by the detector 110 and output a voltage according to the integration result. That is, since the amount of current that is changed depending on an amount of X-rays and flows between the common electrode and the bias voltage source 300 may be very small, such a current may be accumulated and a control signal may be output by the integrator 121.

The compensator 122 may compensate for an output of the integrator 121 wherein the output is influenced by an offset of a current flowing between the common electrode and the bias voltage source 300. That is, even when X-rays are not emitted, a current flowing between the common electrode and the bias voltage source 300 may have an offset value. In this case, since the detector 110 outputs a voltage depending on the offset of the current and the integrator 121 integrates and accumulates such a voltage, even when X-rays are not emitted, the output of the integrator 121 may be gradually saturated.

Accordingly, the compensator 122 may compensate for the output of the integrator 121, wherein the output is influenced by the offset of the current. For example, the compensator 122 may perform the compensation by providing a voltage corresponding to an output value of the detector 110 to one of the input electrodes of the integrator 121, wherein the output value corresponds to an offset of the current.

That is, one of the input electrodes of the integrator 121 may be connected to an output electrode of the detector 110, and at this point, when the integrator 121 is reset, an output electrode of the integrator 121 has a voltage that is the same as that of the output electrode of the detector 110. In other words, the output electrode of the integrator 121 has a voltage corresponding to an output value of the detector 110, wherein the output value corresponds to the offset of the current. At this point, when a corresponding voltage is applied to the other input electrode of the integrator 121 and maintained, even when a reset operation of the integrator 121 is finished, the input electrode and the output electrode of the integrator 121 maintain the same voltage (a voltage corresponding to an output value of the detector 110 corresponding to an offset of a current). Accordingly, since a current flowing between the common electrode and the bias voltage source 300 due to X-rays not being changed and the integrator 121 does not perform accumulation when an offset value is maintained, an output of the integrator 121 is not saturated.

The offset processor 123 may offset a voltage according to an integration result of the integrator 121 by an offset voltage due to the compensator 122. That is, as can be seen in the above-described operation of the compensator 122, the output electrode of the integrator 121 basically has an offset voltage (a voltage corresponding to an output value of the detector 110 corresponding to an offset of a current).

However, since such an offset voltage may limit the dynamic range of the post processor, the offset voltage has to be canceled, and the offset processor 123 may offset such an offset voltage.

The comparator 124 may compare a voltage according to an integration result of the integrator 121 and a reference value, and output a comparison result as an AEC signal. For example, when a voltage according to an integration result of the integrator 121 is greater than the reference value, the comparator 124 may output a signal of high 1, and such a high signal may be an AEC signal for stopping X-ray emission. That is, since a voltage input to the comparator 124 is changed depending on an amount of X-ray exposure, such a voltage and the reference value may be compared and the AEC signal may be output. In this case, the AEC processing unit 100 may output the AEC signal as a digital type signal.

In addition, here, the reference value may be determined by a potentiometer and the like, and a controller and the like of the X-ray imaging system may be designed to change such a reference value.

Meanwhile, an operation of the AEC processing unit 100 will be more specifically described with reference to FIG. 6.

When there is an offset of a current flowing between the bias voltage source 300 and the common electrode and a reset switch and a sample switch are closed, $V_1$, $V_2$, $V_3$, $V_4$, and $V_5$ all have an offset voltage. Then, even when the reset switch and the sample switch are opened, the offset voltage of a positive input (+) of the integrator 121 is maintained by a capacitor of the compensator 122. At this point, since the offset voltages of the $V_3$ and the $V_5$ are also maintained, charges are not accumulated in $C_1$.

However, when a current flowing between the bias voltage source 300 and the common electrode is changed depending on the amount of X-ray exposure, since a voltage output by the detector 110 is changed, the integrator 121 is operated and an amount of X-ray exposure may be checked.

Meanwhile, since $V_6$ has the same voltage level and a polarity opposite to that of the offset voltage, a current flowing between the bias voltage source 300 and the common electrode is not changed, and when values of $R_1$ and $R_2$ are the same, a sum of a current flowing through $R_1$ (a current flowing from $V_5$ to $V_7$) and a current flowing through $R_2$ (a current flowing from $V_6$ and $V_7$) is zero. Accordingly, a voltage of $V_8$ is zero. That is, the offset processor 123 performs a function of offsetting by an offset voltage.

While the above-described states of the voltages of all nodes are maintained, when the amount of X-ray exposure is increased, that is, a current flowing between the bias voltage source 300 and the common electrode is increased, the voltage of $V_5$ is decreased by an operation of the integrator 121, and accordingly a current flowing through the $R_1$ is decreased. However, since a current flowing through $R_2$ is maintained, a voltage of $V_8$ is increased finally.

Accordingly, the voltage applied to the comparator 124 is changed depending on an amount of X-ray exposure, and thus comparator 124 may compare an applied voltage and a reference value and output an AEC signal as a digital type signal.

Meanwhile, as illustrated in FIG. 6, the detector 110 may include a switch 111 that may bypass a current flowing between the bias voltage source 300 and the common electrode. Such a switch 111 may be opened or closed depending on an operation state of the X-ray detector.

That is, the operation of the X-ray detector may be classified into an integration process, a readout process, and the like. Although reading an electric signal output from the pixel part 200 by the gate driver 500, the readout circuit 400, and the like is performed in the readout process, since an AEC is performed in the integration process, the switch 111 is opened in the integration process and closed in the readout process, and may serve to detect a current flowing through resistance RS with high sensitivity in the integration process and decrease voltage drop due to a current flowing between the common electrode and the bias voltage source 300 in the readout process.

Meanwhile, as shown in FIGS. 5 and 7, the output unit 120 may also include an amplifier 125 instead of the comparator 124, and in this case, the output unit 120 may output an AEC signal as an analog type signal. That is, since operations of units prior to the amplifier 125 are the same as those of the above-described operations, the amplifier 125 may amplify a voltage according to an integration result and output the amplified voltage as an AEC signal, and the total system may also be designed such that a controller and the like of an X-ray imaging system receives such an analogue signal and estimates an amount of X-ray exposure by itself.

Figure 3:
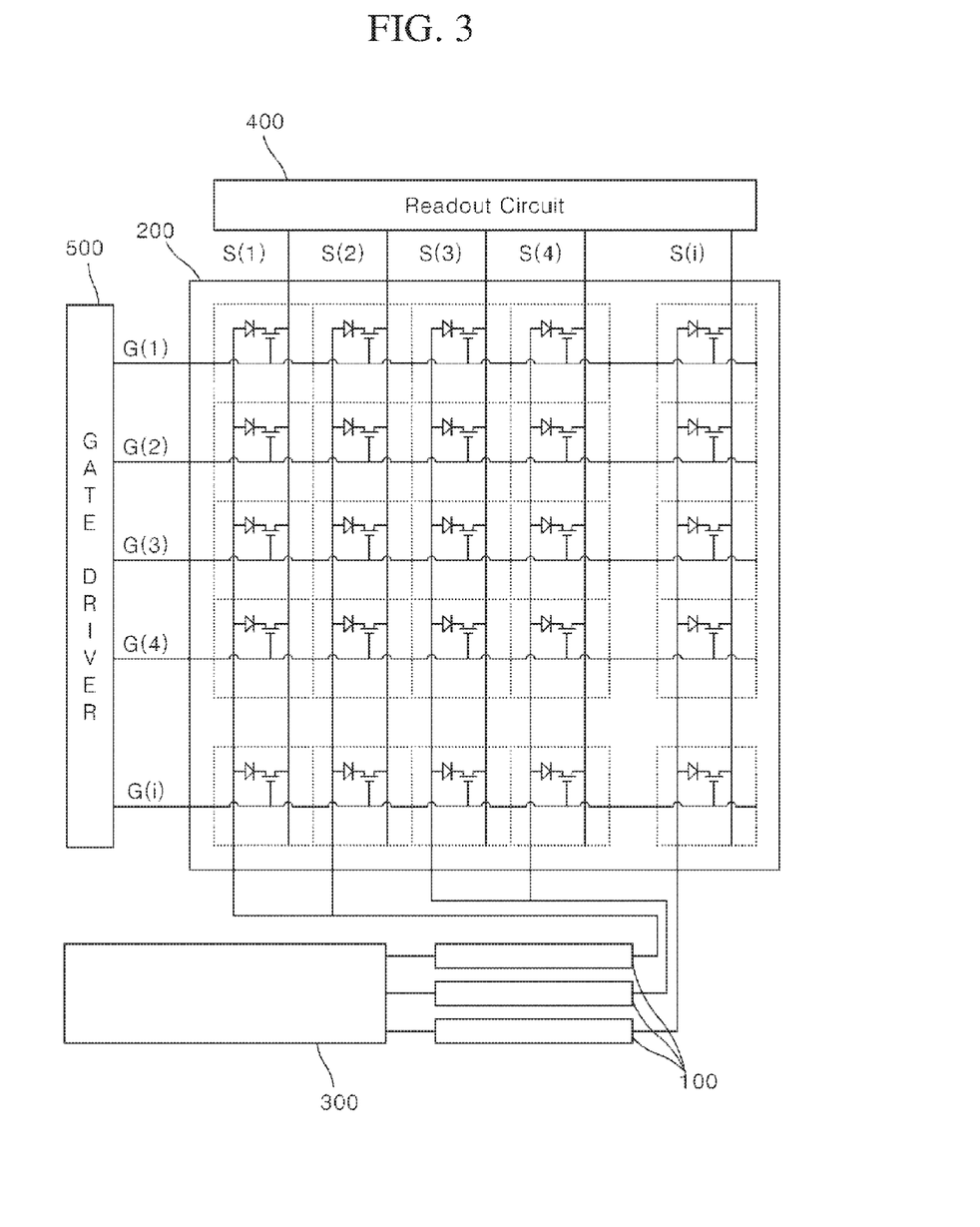
FIG. 3 is a schematic view for illustrating a configuration of an X-ray imaging apparatus according to another embodiment of the present invention.

Meanwhile, FIG. 3 is a schematic view for illustrating a configuration of an X-ray imaging apparatus according to another embodiment of the present invention. As illustrated in FIG. 3, a common electrode may be divided into several groups, and each of the groups may include an AEC processing unit 100. That is, the pixel part 200 may be classified into several regions, an amount of X-ray exposure may be estimated for each of the regions, and a system may also be designed to perform an AEC using an estimated value for a region of interest.

Accordingly, the X-ray imaging apparatus according to the embodiment of the present invention can perform the AEC function without adding additional device or changing the structure of a conventional X-ray detector by performing an AEC function through an AEC processing unit that detects a current flowing between the bias voltage source and the pixels and outputs an AEC signal.

The present invention has been described with reference to the examples illustrated in the drawings, but these are only examples. It will be understood by those skilled in the art that various modifications and equivalent other examples may be made. Therefore, the scope of the present invention is defined by the appended claims.

What is claimed is:

1. An X-ray imaging apparatus comprising:
a bias voltage source that provides a bias voltage to pixels that detect X-rays; and
an automatic exposure control (AEC) processing unit that detects a current flowing between the bias voltage source and the pixels and outputs an AEC signal,
wherein the bias voltage source provides the bias voltage to photodiodes included in the pixels through a common electrode, and the AEC processing unit detects a current flowing between the common electrode and the bias voltage source,
wherein the AEC processing unit includes:
a detector that detects the current and converts into a voltage signal; and
an output unit that outputs an AEC signal depending on a voltage output by the detector,
wherein the detector includes a switch that allows bypassing the current, and
wherein the switch is configured to be open when the X-ray imaging apparatus performs an integration process and closed when the X-ray imaging apparatus performs a readout process.

2. The X-ray imaging apparatus of claim 1, wherein the output unit includes:
an integrator that integrates the voltage and outputs a voltage according to the integration result; and
a comparator that compares the voltage according to the integration result and a reference value and outputs the comparison result as the AEC signal.

3. The X-ray imaging apparatus of claim 2, wherein the output unit further includes a compensator that compensates for an output of the integrator due to an offset of the current.

4. The X-ray imaging apparatus of claim 3, wherein the compensator provides a voltage corresponding to an output value of the detector corresponding to an offset of the current, to any one of input electrodes of the integrator.

5. The X-ray imaging apparatus of claim 3, wherein the output unit further includes an offset processor that offsets the voltage according to the integration result by an offset voltage due to the compensator.

6. The X-ray imaging apparatus of claim 1, wherein the output unit includes:
an integrator that integrates the voltage and outputs a voltage according to the integration result; and
an amplifier that amplifies the voltage according to the integration result and outputs the amplified voltage as the AEC signal.

7. The X-ray imaging apparatus of claim 6, wherein the output unit further includes a compensator that compensates for an output of the integrator due to an offset of the current.

8. The X-ray imaging apparatus of claim 7, wherein the compensator provides a voltage corresponding to an output value of the detector corresponding to an offset of the current, to any one of input electrodes of the integrator.

9. The X-ray imaging apparatus of claim 7, wherein the output unit further includes an offset processor that offsets the voltage according to the integration result by an offset voltage due to the compensator.

10. The X-ray imaging apparatus of claim 1, wherein the common electrode is classified into a plurality of groups, and the AEC processing unit is included in each of the groups.

11. An X-ray imaging apparatus comprising:
a bias voltage source that provides a bias voltage to pixels that detect X-rays; and
an automatic exposure control (AEC) processing unit that detects a current flowing between the bias voltage source and the pixels and outputs an AEC signal,
wherein the AEC processing unit includes a detector that detects the current and converts into a voltage signal, and an output unit that outputs an AEC signal depending on a voltage output by the detector,
wherein the output unit includes an integrator that integrates the voltage and outputs a voltage according to the integration result, and a compensator that provides a voltage corresponding to an output value of the detector corresponding to an offset of the current to the integrator,
wherein the integrator includes an operational amplifier, an integration capacitor, and a reset switch,
wherein a first input electrode of the operational amplifier is connected to an output electrode of the detector, the integration capacitor is connected between the first input electrode and an output electrode of the operational amplifier, and the reset switch is arranged in parallel with the integration capacitor,
wherein the compensator includes an operational amplifier, a sample switch, and a sample capacitor,
wherein the sample switch is connected between the output electrode of the detector and a second input electrode of the operational amplifier of the compensator, the sample capacitor is connected between the second input electrode of the operational amplifier of the compensator and a ground, and an output electrode of the operational amplifier of the compensator is connected to a third input electrode of the operational amplifier of the integrator, and
wherein the reset switch and the sample switch are configured to be closed and then opened, before the X-ray imaging apparatus performs an integration process.

12. The X-ray imaging apparatus of claim 11, wherein the output unit further includes a comparator that compares the voltage according to the integration result and a reference value and outputs the comparison result as the AEC signal.

13. The X-ray imaging apparatus of claim 11, wherein the output unit further includes an amplifier that amplifies the voltage according to the integration result and outputs the amplified voltage as the AEC signal.

\* \* \* \* \*